(12) United States Patent
Dobashi

(10) Patent No.: US 7,489,333 B2
(45) Date of Patent: Feb. 10, 2009

(54) OPHTHALMOLOGIC IMAGE PICKUP APPARATUS

(75) Inventor: Yasuhiro Dobashi, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 886 days.

(21) Appl. No.: 10/858,250

(22) Filed: Jun. 1, 2004

(65) Prior Publication Data

US 2004/0263677 A1 Dec. 30, 2004

(30) Foreign Application Priority Data

Jun. 20, 2003 (JP) ............................ 2003-176346

(51) Int. Cl.
*H04N 3/36* (2006.01)
(52) U.S. Cl. ........................ 348/78; 351/206
(58) Field of Classification Search ............... 348/78; 351/206
See application file for complete search history.

(56) References Cited

U.S. PATENT DOCUMENTS

| 5,555,039 | A | * | 9/1996 | Iki et al. ............... 351/205 |
| 2003/0071966 | A1 | * | 4/2003 | Matsumoto ............ 351/206 |
| 2004/0095554 | A1 | * | 5/2004 | Ono ..................... 351/206 |

FOREIGN PATENT DOCUMENTS

| JP | 02055031 | 2/1990 |
| JP | 04092640 | 3/1992 |
| JP | 04-317626 | 11/1992 |
| JP | 04317626 | 11/1992 |
| JP | 2000-333906 | 12/2000 |
| JP | 2000333906 | 12/2000 |

OTHER PUBLICATIONS

Korean Search Report.
Japanese translation of Chinese Patent Office Communication dated Aug. 18, 2006 concerning Chinese Patent Application No. 2004100423248. (2 pp).
European Search Report Oct. 20, 2004.
European Patent Office, Official Letter Search Report dated Jul. 23, 2007 concerning Application No. 04 013 176.5 (4 pages).

* cited by examiner

*Primary Examiner*—Young Lee
*Assistant Examiner*—Richard Torrente
(74) *Attorney, Agent, or Firm*—Morgan & Finnegan, LLP

(57) ABSTRACT

A fundus camera for performing fluorescent image pickup is provided. A timer is started when a fluorescent agent is infused into a body, and a mode of an amplifying ratio control part is set to AGC. AGC is then checked, and fluorescent illuminance of respective eyes to be examined are calculated, if the AGC is operating. A fluorescent illuminance value at a fundus is calculated from a gain value on the AGC and a corresponding time which are stored in an amplifying ratio memory, thereby determining a proper exposure value. When the AGC is not operating, the fluorescent illuminance value is calculated from the calculated illuminance curves of the respective eyes to be examined and an output of a timer, thereby determining a proper exposure value. When an image pickup switch is depressed while observing an image, input from the image pickup switch is detected.

3 Claims, 10 Drawing Sheets

Description
1. observation light source
4. image pickup light source
13. image pickup element
21. stored charge reading part
22. amplifying part
23. image signal processing part
24. system control part
24a. first calculation means
24b. second calculation means
24c. exposure determination control means
25. display part
26. amplifying ratio control part
27. image pickup switch
28. timer means
29. light source control part
30. amplifying ratio memory
31. illuminance normalization means
32. image recording means

FIG. 1

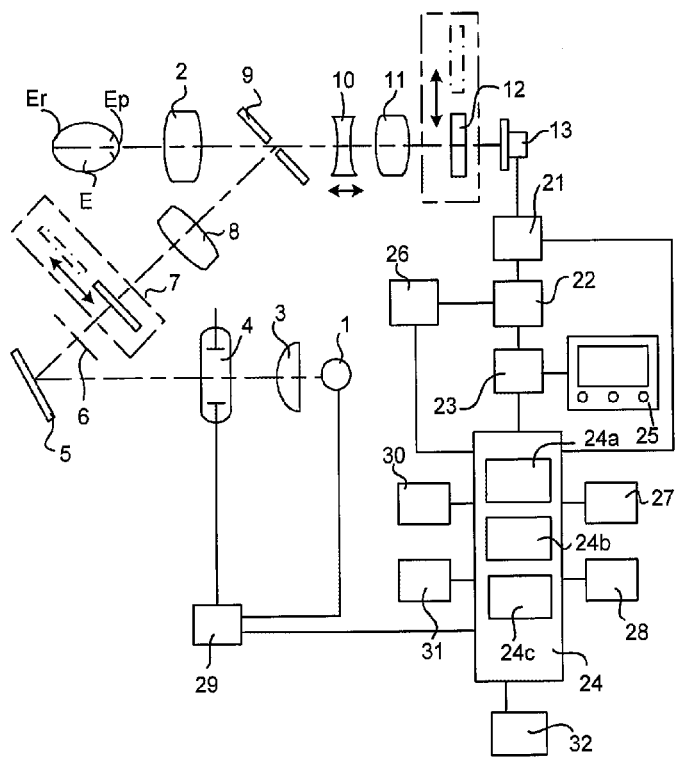

Description

1. observation light source
4. image pickup light source
13. image pickup element
21. stored charge reading part
22. amplifying part
23. image signal processing part
24. system control part
24a. first calculation means
24b. second calculation means
24c. exposure determination control means
25. display part
26. amplifying ratio control part
27. image pickup switch
28. timer means
29. light source control part
30. amplifying ratio memory
31. illuminance normalization means
32. image recording means

OPHTHALMOLOGIC IMAGE PICKUP APPARATUS

BACKGROUND OF THE INVENTION

1. Field of the Invention

The present invention relates to an ophthalmologic image pickup apparatus used in an ophthalmologic doctor's office or the like.

2. Related Background Art

Up to now, there has been known an apparatus that picks up an image of an eye to be examined using an image pickup element, which is represented by a CCD, to convert the image into an image signal, thereby performing observation and image pickup on the eye to be examined. In particular, when performing infrared fluorescent image pickup by using a fundus camera, a fundus cannot be observed through an optical finder. Therefore, alignment and focusing are performed using the above-mentioned image pickup element.

In general, a phase of contrast in the fluorescent image pickup is classified into an initial phase of contrast, a middle phase of contrast, and a later phase of contrast. The initial phase of contrast is a first period from the start of choroid contrast to the completion of contrast of a choroid vein. The middle phase of contrast is a subsequent period from the completion of contrast of the choroid vein to the loss of a fluorescent agent from the choroid vein. The later phase of contrast is a final period during which a diffuse choroid background fluorescence is observed.

In the initial phase of contrast, a fluorescent agent injected (hereinafter merely referred to as "infused") into a vein of a person to be examined reaches a thick blood vessel of a fundus by blood circulation. As the phase of contrast becomes the middle phase of contrast and then the later phase of contrast, the fluorescent agent gradually penetrates a thin blood vessel with the lapse of time. Therefore, a concentration of the fluorescent agent present in a blood vessel in the initial phase of fluorescent contrast becomes much higher than the concentration of the fluorescent agent present in the blood vessel in the later phase of fluorescent contrast. Thus, because of the circulation of the fluorescent agent, a fluorescent illuminance of the eye to be examined in the initial phase of contrast is much higher than the fluorescent illuminances of the eye to be examined in the middle phase of contrast and the later phase of contrast. In addition, a change in illuminance in the initial phase of contrast becomes larger than the changes in illuminance in the middle phase of contrast and the later phase of contrast.

In general, a dynamic range of a fluorescent illuminance of a fundus is very wider than the dynamic range of an image pickup element. Therefore, in either cases where the fluorescent illuminance is low or the fluorescent illuminance is high, it is hard to control an observation light intensity, an image pickup light intensity, a gain of the image pickup element, and the like, with the result that it is difficult to perform image pickup with preferable image quality.

In order to solve such a problem, there has been proposed a method using an auto gain control (AGC) capable of obtaining a constant image signal, even if the fluorescent illuminance of the eye to be examined has been changed. In this method, when fluorescent observation is performed, the AGC is operated and controlled so that an average value of an image signal from an image of the eye to be examined is kept constant, even if the brightness of the eye to be examined, that is, the observation light intensity has been changed. On the other hand, when fluorescent image pickup is performed, a light emission time of an image pickup light source is as short as several milli-seconds. Even if the AGC is operated, the gain cannot be followed. Therefore, to constantly obtain a proper image of the eye to be examined, a gain of an image signal from the image pickup element is changed from the AGC to a fixed gain at image pickup timing and the image pickup light intensity is controlled according to the brightness of the eye to be examined.

Also, there has been proposed an image pickup method as described in Japanese Patent Application Laid-Open No. H02-124137. According to the image pickup method, a timer for detecting an elapsed time from the infusion of a fluorescent agent is provided. When a signal indicating the elapsed time from the timer is received, an image pickup light emission intensity is increased with an elapsed time from the infusion.

The method using the AGC according to the above-mentioned conventional examples is effective to the case of initial image pickup for the fundus observation, in which the fluorescent illuminance at the fundus is high. However, in the later phase in which the fluorescent illuminance value significantly reduces, it is necessary to prepare a high sensitive image pickup element or an observation light source having a large light emission intensity. Therefore, there is a disadvantage in that a size of an apparatus becomes larger or a cost of a system becomes higher. In addition, when a sensitivity of the image pickup element is not sufficiently high, the AGC is not operated. Therefore, there is another disadvantage in that a gain at a time when the AGC is changed to the fixed gain and a proper exposure value of the image pickup light intensity cannot be obtained in the image pickup.

In the method as described in Japanese Patent Application Laid-Open H02-124137, a fluorescent illuminance at the fundus, which changes with a lapse of time significantly varies according to personal differences such as age, sex, weight, and height, an infused fluorescent agent amount, an infusion rate, a disease of a patient, or the like. Therefore, in the method of increasing the image pickup light intensity based on only the elapsed time from the infusion, there is a disadvantage in that a halation in the initial phase and a poor contrast in the later phase cannot be avoided.

SUMMARY OF THE INVENTION

The present invention has been made to solve the above-mentioned problems. An object of the present invention is to provide an ophthalmologic image pickup apparatus capable of automatically setting a proper exposure value using an inexpensive apparatus without using a high sensitive image pickup element or an expensive apparatus.

In order to achieve the above-mentioned object, an ophthalmologic image pickup apparatus according to the present invention includes:

an observation illumination light source;

an image pickup illumination light source;

an illumination optical system for projecting observation illumination light and image pickup illumination light to an eye to be examined;

timer means for measuring an image pickup elapsed time for the eye to be examined;

image pickup means for picking up reflection light on the eye to be examined as an image of the eye to be examined through an observation and image pickup optical system;

image pickup exposure control means for controlling at least one of the image pickup illumination light source and the image pickup means having an amplifying ratio;

illuminance detecting means for detecting an illuminance value of the eye to be examined from at least one of an image signal from the image pickup means and the amplifying ratio of the image pickup means;

a first calculation means for calculating illuminance-time information relating an output from the illuminance detecting means to an output from the timer means;

a second calculation means for calculating a function of time information based on an output from the first calculation means; and exposure determination and control means for determining an exposure value based on the output from the timer means and at least one of a calculation result from the first calculation means and a calculation result from the second calculation means.

BRIEF DESCRIPTION OF THE DRAWINGS

FIG. 1 is a structural diagram showing a fundus camera according to an embodiment of the present invention;

DESCRIPTION OF THE PREFERRED EMBODIMENT

Figure 2:
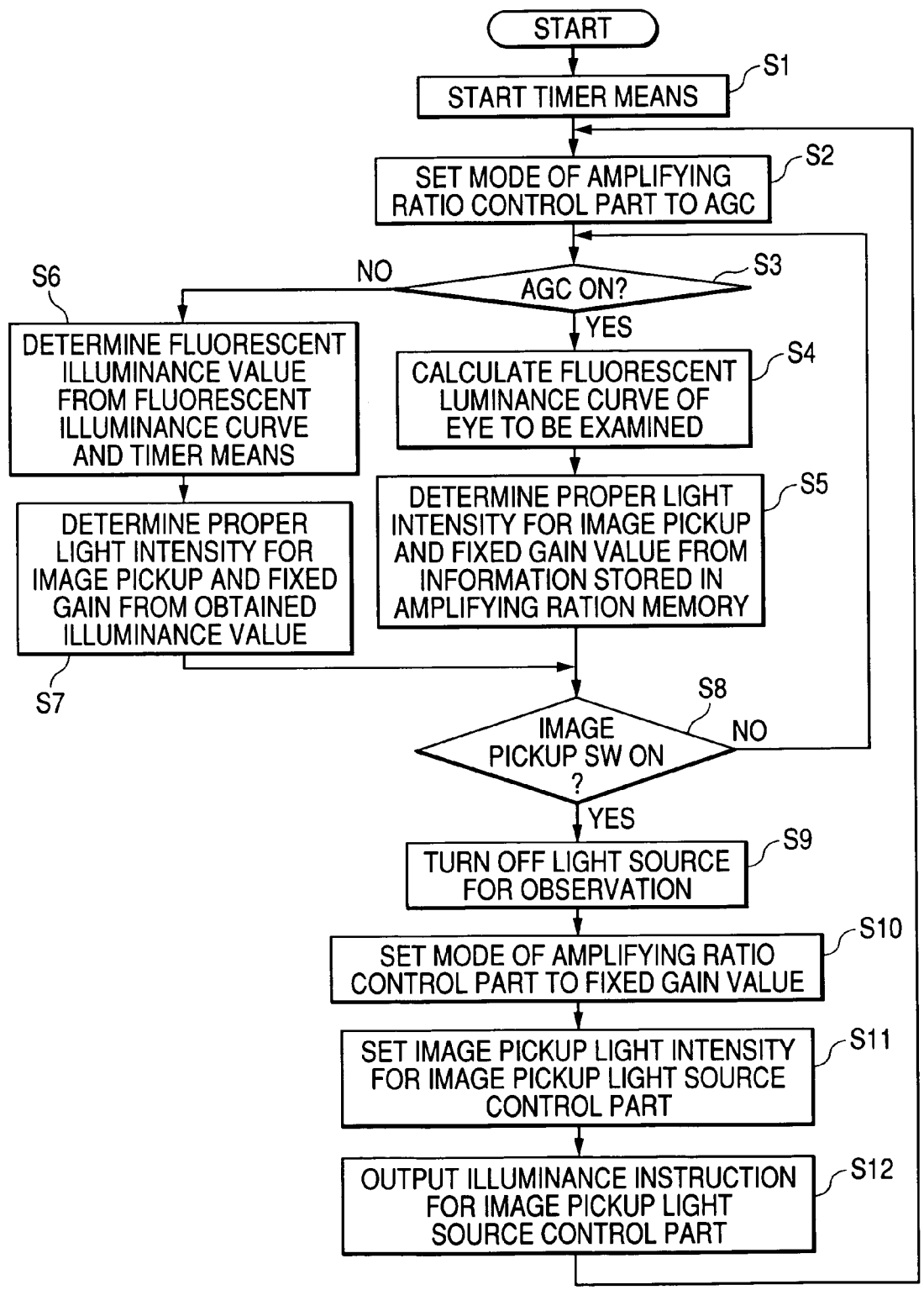
FIG. 2 is a flow chart showing an operation of a system control part.

The present invention will be described in detail with reference to an embodiment shown in the drawings.

FIG. 1 is a structural diagram showing a fundus camera according to an embodiment of the present invention. A condenser lens 3, an image pickup light source 4, a mirror 5, a diaphragm 6 having a ring opening, an infrared fluorescent exciter filter 7 which is insertable to an optical path, a relay lens 8, and a holed mirror 9 are disposed in order on an optical path between an observation light source 1 and an objective lens 2, thereby composing a fundus illumination optical system. A focal lens 10, an image pickup lens 11, an infrared fluorescent barrier filter 12 which blocks excitation light, transmits only fluorescence, and is insertable to an optical path, and an image pickup element 13 are disposed in a fundus observation and image pickup optical system behind the holed mirror 9.

An output of the image pickup element 13 is connected with a system control part 24 through a stored charge reading part 21, an amplifying part 22, and an image signal processing part 23. The image signal processing part 23 is connected with a display part 25. The system control part 24 includes a first calculation means 24a, a second calculation means 24b, and exposure determination control means 24c. The system control part 24 is connected with the stored charge reading part 21, an amplifying ratio control part 26, an image pickup switch 27, timer means 28, a light source control part 29 for observation and image pickup, which controls the observation light source 1 and the image pickup light source 4, an amplifying ratio memory 30, illuminance normalization means 31, and image recording means 32 composed of, for example, a hard disk, an MO, a Zip, a Jazz, CD-R/RW, DVD-RAM, DVD±R/RW, a semiconductor memory.

A light flux emitted from the observation light source 1 is reflected on the mirror 5 through the condenser lens 3 and the image pickup light source 4. Reflection light on the mirror 5 transmits through the ring diaphragm 6, the infrared fluorescent exciter filter 7, and the relay lens 8 and reflected on the vicinity of the holed mirror 9. Then, the light transmits through the objective lens 2 and a pupil Ep of an eye to be examined E to illuminate a fundus Er. An image of the eye to be examined, which is produced by the illumination transmits through the pupil Ep, the objective lens 2, an opening of the holed mirror 9, the focal lens 10, the image pickup lens 11, and the infrared fluorescent barrier filter 12 and is formed onto the image pickup element 13.

A stored charge after photoelectric conversion is maintained in the image pickup element 13. The stored charge reading part 21 outputs a read signal to the image signal processing part 23 through the amplifying part 22 during reading of the stored charge and clearing of the maintained charge in succession. The image signal processing part 23 performs processing necessary to output to the display part 25, so that an observation image at this time is displayed on the display part 25. Note that the image pickup element 13 has a sensitivity required for at least observation and image pickup in the initial phase of fluorescent contrast.

FIG. 2 is a flow chart showing an operation of the system control part 24 at the time of image pickup. First, in Step S1, when the fluorescent agent is infused into a body, the timer means 28 is started by an operator. In the initial phase of fluorescent contrast, the fluoresce illuminance at the fundus Er significantly changes. Therefore, in step S2, a mode of the amplifying ratio control part 26 is set to AGC so as to perform an adequate fundus observation without resetting a light intensity of the observation light source 1 in each case even if the brightness of the fundus Er changes.

The AGC performed by the amplifying ratio control part 26 is a control for keeping an average value of image output data constant by the feedback of the image output data. In practice, two-dimensional image data is used. In this embodiment, an AGC function will be described using simple one-dimensional image data.

Figure 3A:
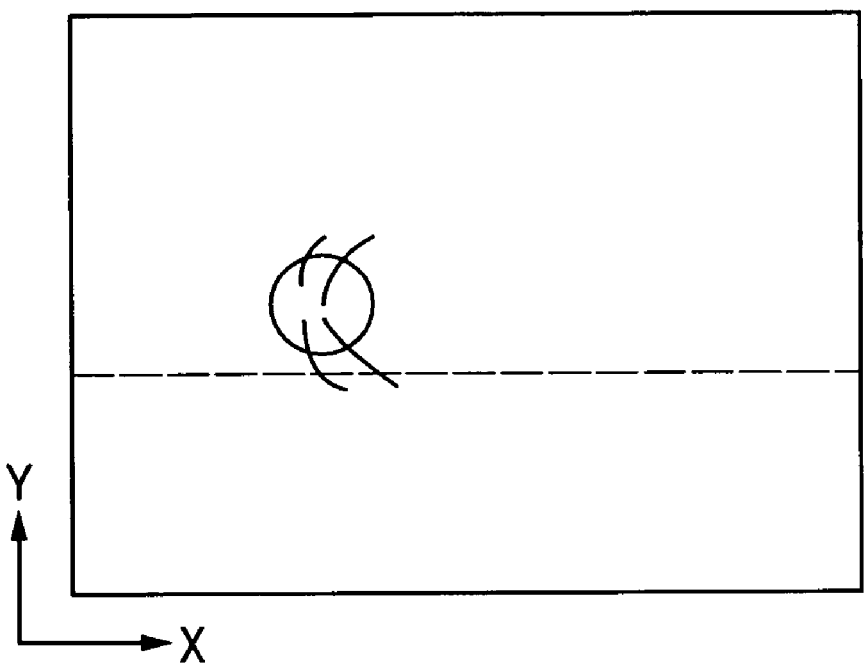
FIGS. 3A and 3B are explanatory diagrams showing a fundus image immediately after appearance of a fluorescent agent and an AGC.
Figure 3B:
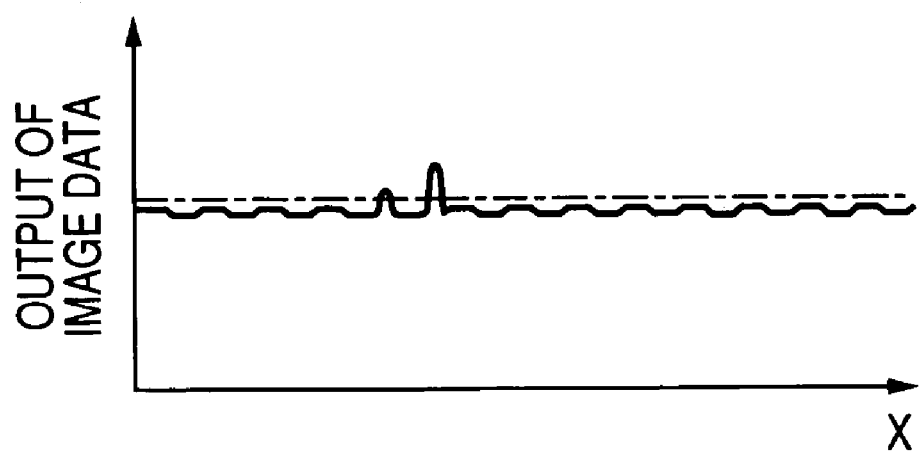
Figure 4A:
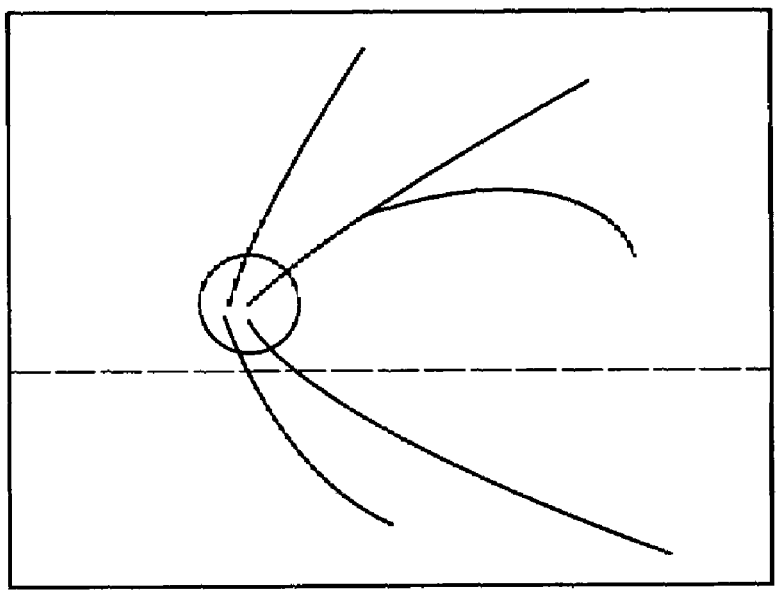
FIGS. 4A and 4B are explanatory diagrams showing a fundus image with a state in which the fluorescent agent spreads and the AGC.
Figure 4B:
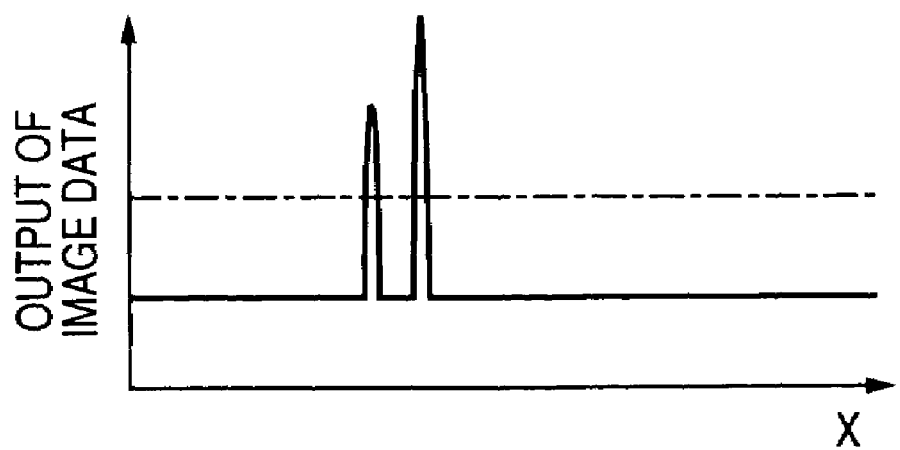

FIG. 3A shows a fundus image immediately after appearance of a fluorescent agent from a papilla. FIG. 4A shows a fundus image with a state in which the fluorescent agent spreads on arteries of a choroid and a retina. FIG. 3B shows an output from the amplifying ratio control part 26 along a fundus line indicated by a dot line in FIG. 3A in the corresponding state. FIG. 4B shows an output from the amplifying ratio control part 26 along a fundus line indicated by a dot line in FIG. 4A in the corresponding state. The AGC is performed so as to keep an average output value of respective points on the fundus line constant. A line indicated by a chain line in each of FIGS. 3B and 4B shows the average output value.

As shown in FIG. 3B, in a state immediately after the appearance of the fluorescent agent from the papilla, the fluoresce illuminance is not sufficiently high yet. Therefore, the gain is increased by the AGC. On the other hand, in the case of FIG. 4B, the fluoresce illuminance becomes higher. Therefore, in order to keep the average output value constant, the gain is controlled to be low.

In Step S3 shown in FIG. 2, whether or not the AGC is operating is checked. When the AGC is operating, the control proceeds to Step S4 to calculate a fluoresce illuminance curve of the eye to be examined E. Note that a calculated result is not used while the AGC is operating.

The image pickup element 13 used in this embodiment has a sensitivity sufficient for the initial phase of fluorescent contrast. In the starting of the fluorescent image pickup, the fluorescent agent does not appear at the fundus yet. Therefore, there is no light that transmits through the infrared fluorescent barrier filter 12, so that the fundus Er is observed in darkness. Thus, an AGC gain value of the amplifying ratio control part 26 becomes maximum.

Figure 5A:
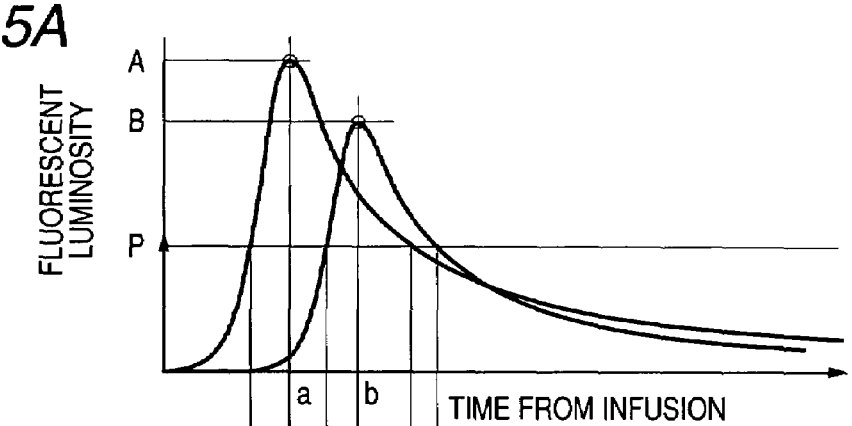
FIGS. 5A and 5B are graphs showing a relationship between a fluorescent illuminance value to an elapsed time from an infusion of the fluorescent agent and a gain value on the AGC.
Figure 5B:
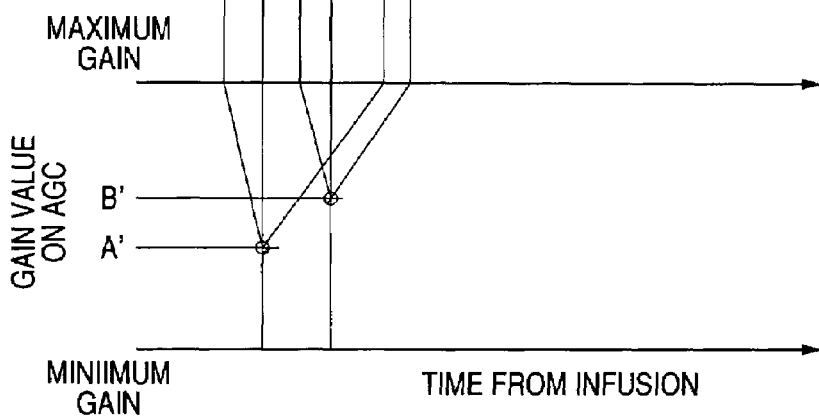

FIGS. 5A and 5B show a change in fluorescent illuminance value at the fundus Er and a change in AGC gain value in the initial phase of fluorescent contrast. FIG. 5A shows a fluorescent illuminance curve of the fluorescent illuminance value with an elapsed time from the infusion of the fluorescent agent at a point on a blood vessel near the papilla at the fundus Er and FIG. 5B shows the AGC gain value at this time. Note that two curves shown in FIG. 5A indicate curves with respect to eyes to be examined A and B of two persons whose ages, sexes, weights, and heights are different from each other.

After the infusion of the fluorescent agent, when the fluorescent illuminance increases with increasing the concentration of the fluorescent agent at the fundus Er, the AGC gain value is reduced so as to keep an average value of a picture output constant. When the fluorescent illuminance reaches a maximum value, the gain value becomes a minimum value. When the fluorescent illuminance reduces, the gain value increases and then reaches a maximum gain value. In FIGS. 5A and 5B, when the fluorescent illuminance becomes an illuminance value P, the gain value reaches the maximum gain value.

Figure 6:
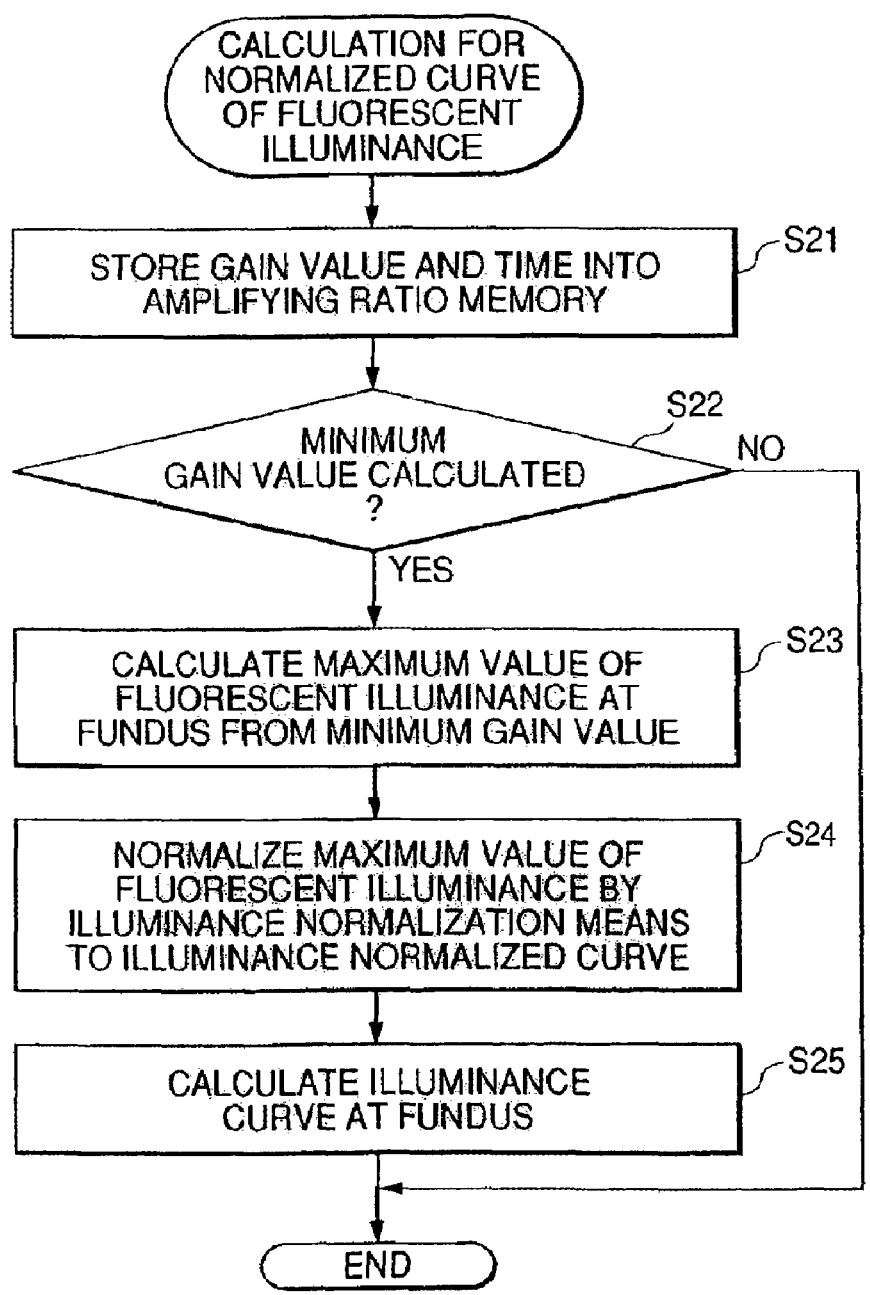
FIG. 6 is a flow chart for calculating a normalized curve of fluorescent illuminance.

FIG. 6 is a flow chart showing a subroutine of Step S4 shown in FIG. 2. In Step S21, the AGC gain value and a corresponding time are stored in the amplifying ratio memory 30. In Step S22, the AGC gain value and the time which are stored in the amplifying ratio memory 30 are checked to detect a minimum gain value. After the detection of the minimum gain value in Step S22, the fluorescent illuminance value of an image at the detected minimum gain value is corrected using a gain in Step S23. Therefore, the maximum value of the fluorescent illuminance at the fundus Er and the corresponding time are calculated.

When FIGS. 5A and 5B are actually viewed, it is apparent from information stored in the amplifying ratio memory 30 that the minimum gain value is obtained in the case where the eye to be examined A is "A', a" and the eye to be examined B is "B', b". When the back calculation is performed based on the gain value, a maximum value of the fluorescent illuminance value and an elapsed time from the starting of image pickup can be calculated. Therefore, calculation results of the first calculation means are as follows.

Information "A', a" detected from the memory 30→calculation result "A, a"

Information "B', b" detected from the memory 30→calculation result "B, b"

Figure 7:
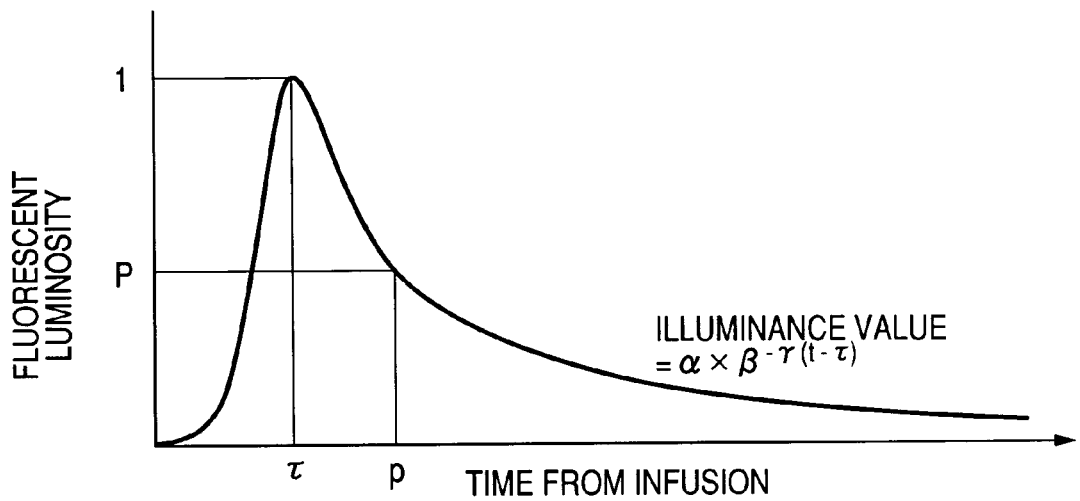
FIG. 7 is a graph showing a normalized curve of the fluorescent illuminance, which is prepared in advance.

FIG. 7 is a graph showing a normalized curve of the fluorescent illuminance which is prepared in advance (S23). The abscissa indicates an elapsed time from the infusion and the ordinate indicates the fluorescent illuminance at the fundus Er. When the fluorescent illuminanee becomes a maximum value "1" at a time τ, the illuminance value in the middle phase of contrast to the later phase of contrast, that is, the illuminance value after a peak of the fluorescent illuminance can be expressed by $\alpha \times \beta^{-\gamma(t-\tau)}$. Here, $\alpha$, $\beta$, $\gamma$, and $\tau$ are arbitrary constants which are obtained from experimental values. In this embodiment, 0.7, 3.5, and 0.003 are used as $\alpha$, $\beta$, and $\gamma$, respectively. $\tau$ indicates an elapsed time after the infusion, which is obtained from the timer means 28.

Figure 8:
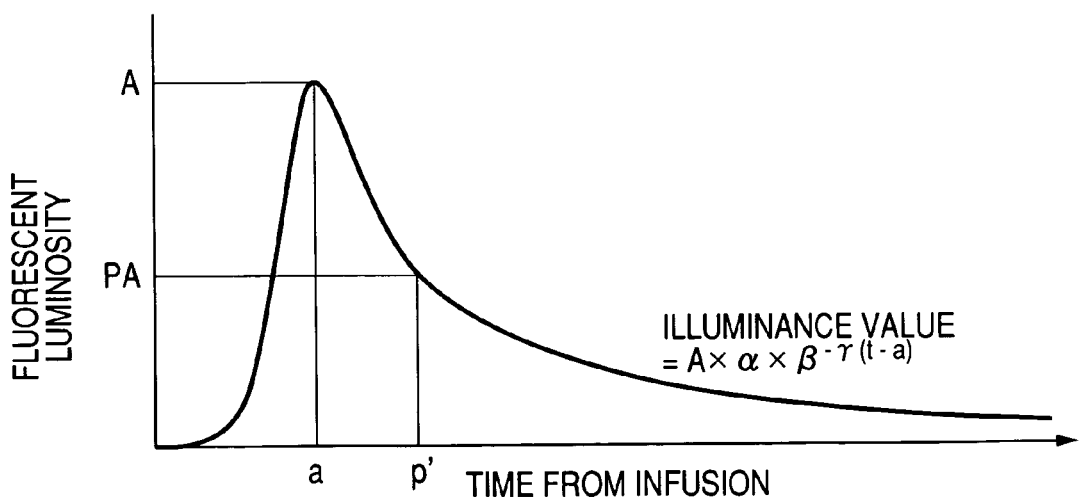
FIG. 8 is a graph showing a normalized curve of an eye to be examined A as shown in FIG. 5, which is normalized by illuminance normalization means.

In Step S24, in order to calculate a fluorescent illuminace curve of the eye to be examined, the calculation result "A, a" is adjusted onto a peak value "1, τ" of the normalized curve of the fluorescent illuminance as shown in FIG. 7 by the illuminance normalization means 31. The illuminance normalization means 31 multiplies the result "A, a" by A in the ordinate direction and performs parallel shift such that "a" coincides with τ in the abscissa direction. According to the illuminance normalization means 31, a fluorescent illuminance curve of the eye to be examined A is calculated by $A \times \alpha \times \beta^{-\gamma(t-a)}$ as shown in FIG. 8. Similarly, a fluorescent illuminance curve of the eye to be examined B is calculated by $B \times \alpha \times \beta^{-\gamma(t-b)}$. The fluorescent illuminance curves obtained here are used as calculation results of the second calculation means in Step S6 shown in FIG. 2.

Next, in Step S5 shown in FIG. 2, the fluorescent illuminance value at the fundus Er is calculated from the gain value on the AGC and the corresponding time which are stored in the amplifying ratio memory 30, thereby determining a proper exposure value. In this embodiment, the proper exposure value is determined using two parameters, a fixed gain value and an image pickup light emission intensity.

When the AGC is not operating in Step S3, that is, when the gain on the AGC reaches the maximum gain as in the case where the fluorescent illuminance is smaller than the illuminance value P as shown in FIG. 5A, even if the fluorescent illuminance at the fundus Er reduces, the gain does not change, so that the fluorescent illuminance cannot be calculated. Therefore, in Step S6, the fluorescent illuminance value at the fundus Er is calculated from each of the fluorescent illuminance curves $A \times \alpha \times \beta^{-\gamma(t-a)}$ and $B \times \alpha \times \beta^{-\gamma(t-b)}$ of the respective eyes to be examined E, which are calculated in Step S24 shown in FIG. 6 and an output of the timer means 28. In Step S7, the proper exposure value is determined. In this embodiment, the two parameters, the fixed gain value and the image pickup light emission intensity are determined.

Hereinafter, an example of a method of calculating the light emission intensity of the image pickup light source 4 and the gain value of the fixed gain from the fluorescent illuminance value at the fundus Er, which is performed by the exposure determination control means in Step S5 and Step S7 will be described with reference to FIG. 9. In this embodiment, the sensitivity of the image pickup element 13 can be changed from 0 dB to 8 dB. The output of the image pickup light source 4 can be changed from a value corresponding to ISO 200 to a value corresponding to ISO 12.5.

The gain value and the image pickup illumination light intensity each are set to a maximum value until the fluorescent illuminance in the initial phase of fluorescent contrast appears. When the fluorescent illuminance appears and an illuminance value of an output image becomes too high, the gain value is first reduced. After the gain value becomes minimum, the illumination light intensity of the image pickup light source 4 is reduced. When the fluorescent illuminance exceeds a maximum value and then becomes lower, the image pickup illumination light intensity is first increased. After the image pickup illumination light intensity becomes maximum, the gain value is increased. This is because a purpose of this embodiment is to obtain a high resolution image-pickup image having a lower noise.

Figure 9:
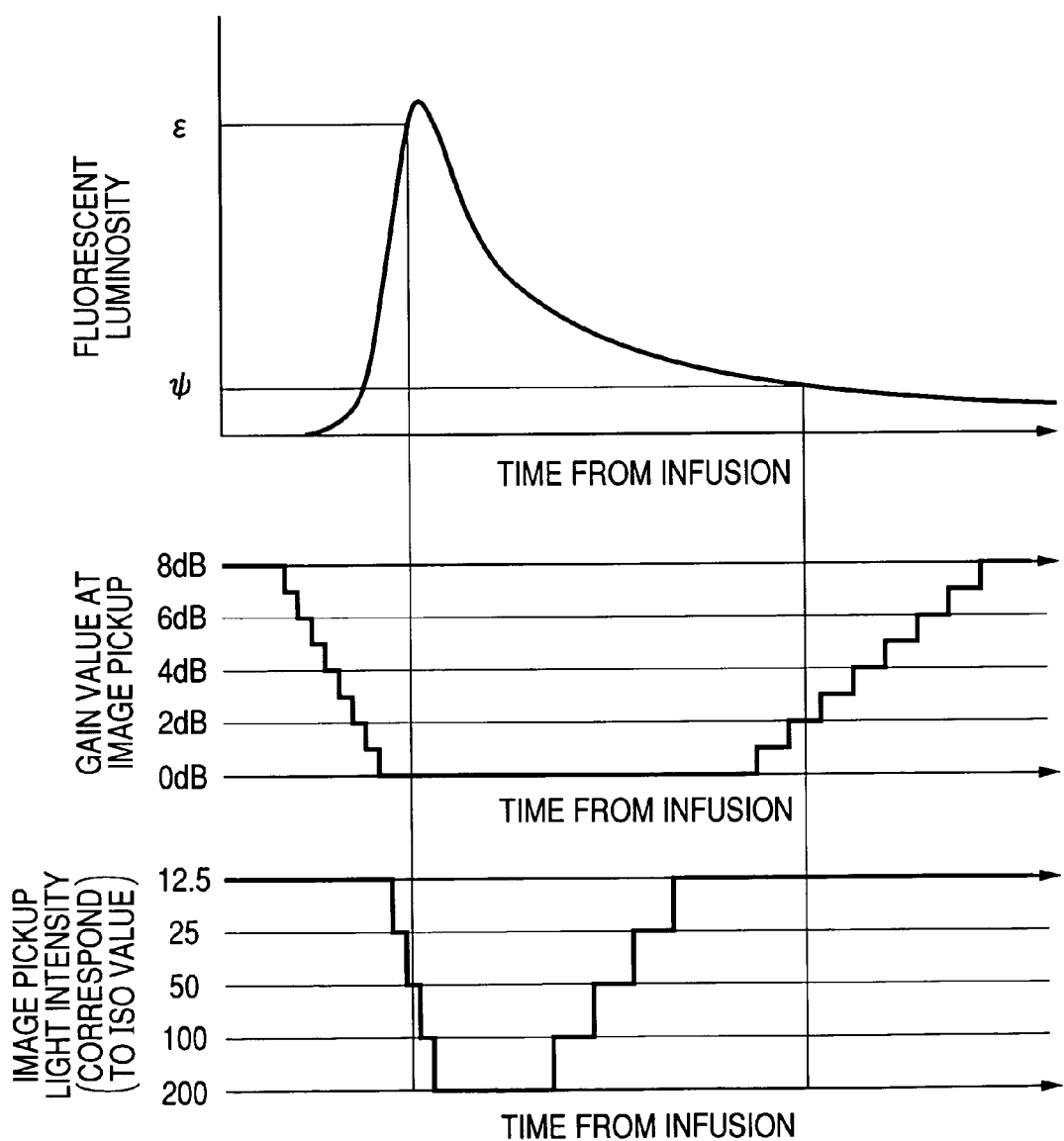
FIG. 9 is a graph for calculating an observation illumination light intensity and a fixed gain value from the fluorescent illuminance value.

In FIG. 9, when the illuminance value is $\epsilon$, the image pickup illumination light intensity and the fixed gain value are calculated as a value corresponding to ISO 50 and a gain of 0 dB, respectively. When the illuminance value is $\phi$, as a result of exposure determination, the image pickup illumination light intensity and the fixed gain value are calculated as a value corresponding to ISO 12.5 and a gain of 2 dB, respectively. The system control part 24 repeats the above-mentioned cycle until the image pickup switch 27 is depressed by a person performing image pickup.

While observing the image on the display part 25, the person performing image pickup performs alignment. After the alignment is completed, the image pickup switch 27 is depressed. The system control part 24 detects an input from the image pickup switch 27 in Step S8 shown in FIG. 2. In Step S9, the observation light source 1 is turned off. After that, in Step S10, a mode of the amplifying ratio control part 26 is set to a fixed gain value. The fixed gain value is set to the value obtained in Step S5 or Step S7.

The reason why the mode of the amplifying ratio control part 26 is switched from the AGC to the fixed gain is as follows. That is, the light emission time of the image pickup light source 4 is several milli-seconds and thus short. Even if the AGC is operated, the gain cannot be followed. Next, in Step S11, the image pickup light intensity of the light source control part 29 for observation and image pickup is set to the value obtained in Step S5 or Step S7.

After all setting operations are completed, in Step S12, a light emission instruction is outputted to the light source control part 29 for observation and image pickup to perform image pickup. After the image pickup is completed, the operation returns to the fundus observation. Therefore, the mode of the amplifying ratio control part 26 is returned to the AGC to complete the image pickup operation.

In this embodiment, in order to obtain the proper exposure value, two values, that is, the amplifying ratio and the image pickup illumination light intensity are set in Step S5 and Step S7 as shown in FIG. 2. Any one of both values may be set.

In this embodiment, after the completion of the image pickup in Step S12, the picked up image is not recorded but the image may be recorded as follows. That is, a read image signal is amplified by the amplifying part 22, converted into a digital signal by an A/D converter (not shown) through the image signal processing part 23, and inputted to the system control part 24. Then, the converted digital image signal is recorded in the image recording means 32 after the operation of Step S12 is completed.

Figure 10:
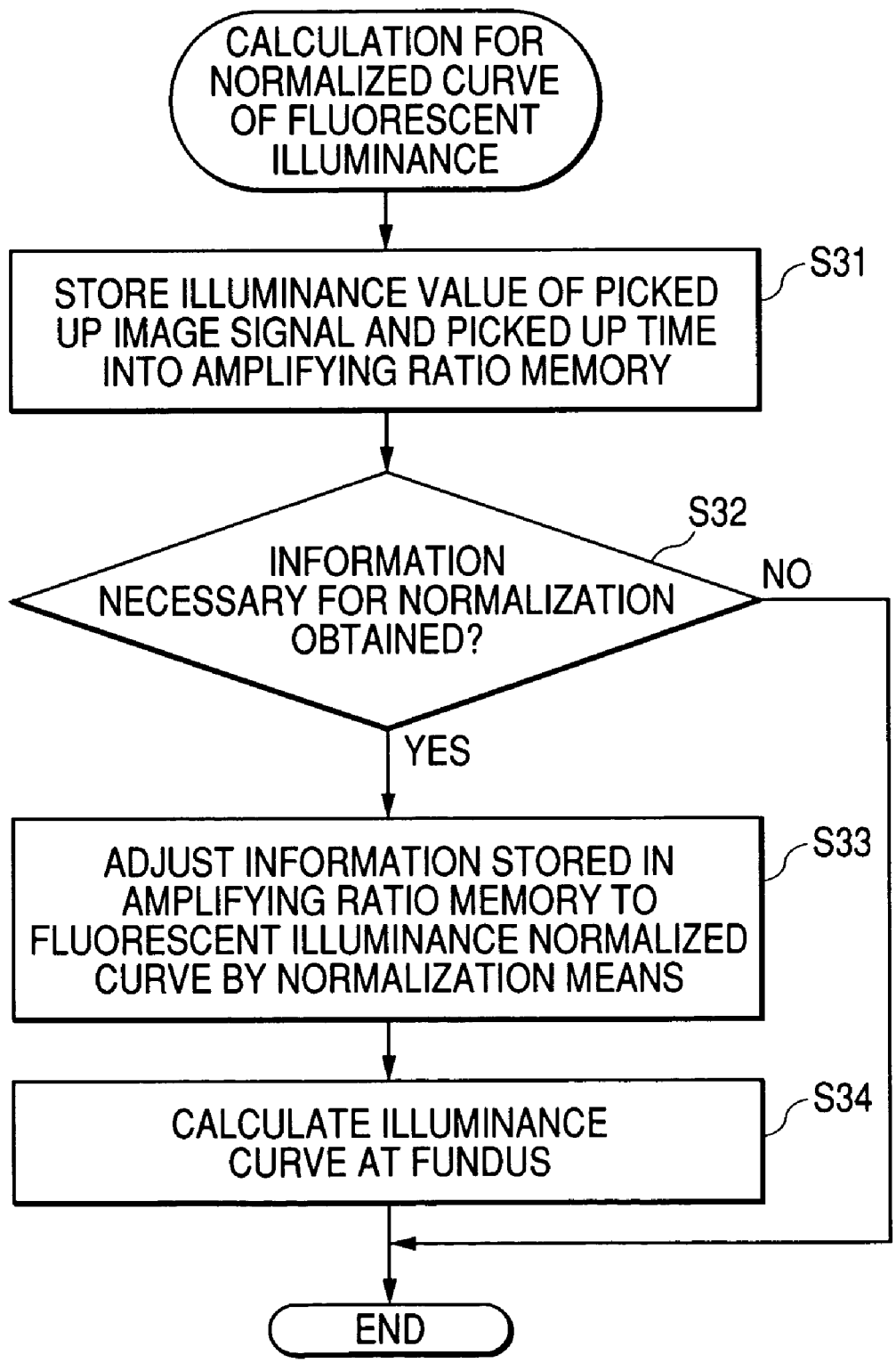
FIG. 10 is a flow chart for calculating a normalized curve of fluorescent illuminance.

In this embodiment, the example in which the illuminance value of each of the eyes to be examined E at the fundus is detected from the amplifying ratio of the image pickup means in Step S4 shown in FIG. 2 is described. Instead of the operation of Step S4, the operation of the flow chart shown in FIG. 10 may be performed. That is, in Step S31, the illuminance value of the picked up image signal and the picked up time in the initial phase of fluorescent contrast, which are stored in the image recording means 32 are stored in the amplifying ratio memory 30. In Step S32, whether the image signal necessary for normalization is obtained or not is checked. In Step S33, the information stored in the amplifying ratio memory 30 is adjusted onto the normalized curve of fluorescent illuminance by the illuminance normalization means 31. In Step S34, a fluorescent illuminance curve is calculated from several information in the initial phase of fluorescent contrast as shown in FIG. 11.

Figure 11:
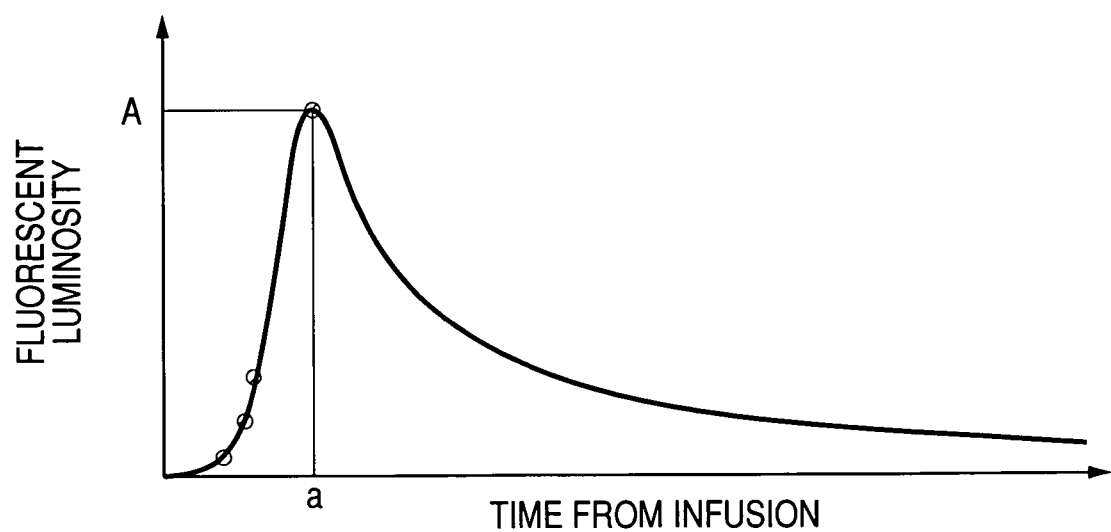
FIG. 11 is a graph showing a fundus illuminance curve normalized using a plurality of sample information.

In FIG. 11, the abscissa indicates an elapsed time from the infusion of the fluorescent agent and the ordinate indicates the fluorescent illuminance value at the fundus. In FIG. 11, each black circle indicates the illuminance value of the picked up image signal and a dot curve indicates the fluorescent illuminance curve at the fundus, which is calculated from the information stored in the amplifying ratio memory 30.

In this embodiment, the example in which the illuminance value of each of the eyes to be examined E at the fundus is detected from the amplifying ratio of the image pickup means in Step S4 shown in FIG. 2 is described. However, the sensitivity of the used image pickup element 13 is low. Therefore, when the observation using the AGC function cannot be performed in the initial phase of contrast or when the amplifying ratio control part 26 is not provided with the AGC function, the image signal illuminance value of the image signal obtained by the image processing part 23 and the corresponding time are stored in the amplifying ratio memory 30, and maximum value information of the fundus illuminance is calculated by the system control part 24. Thus, the fluorescent illuminance curve can be also determined based on a calculation result.

As described above, according to the ophthalmologic image pickup apparatus of the present invention, the function of the fluorescent illuminance value at the fundus using a time as a variable can be obtained from the maximum value of the fluorescent illuminance at the fundus and the corresponding time. When the observation and image pickup light intensity and the gain are estimated from the function of the fluorescent illuminance value, the proper exposure value can be automatically set in fluorescent image pickup.

Further, even when an expensive apparatus which includes an illumination light source having a large light emission intensity, serving as an observation light source is not used or even when a high sensitive image pickup element is not used, the illuminance value at the fundus in the later phase of fluorescent contrast can be estimated. Thus, an image in which no error is caused can be obtained at any time using an inexpensive structure without increasing a size of the apparatus.

What is claimed is:

1. An ophthalmologic image pickup apparatus which picks up an image of a fluorescence of a fluorescent agent in a fundus of an eye of a person to be examined after injecting the fluorescent agent into a vein of the person, comprising:

an observation illumination light source for illuminating the eye of the person when the eye is observed;

an image pickup illumination light source for illuminating the eye of the person when an image of the eye is picked up;

timer means for measuring an elapsed time from injection of the fluorescent agent into the vein of the person;

image pickup means for picking up the image of the eye;

illuminance detecting means for detecting an illiminance value of the eye from at least one of an image signal from the image pickup means and an amplifying ratio of the image pickup means; and calculation means for calculating a predicting formula:

$$\alpha \times \beta^{-\gamma(t-\tau)}$$

used for predicting a variation of the illuminance value of the eye in accordance with the elapsed time after stopping illumination of the eye by the observation illumination light source, on a basis of a relation between the elapsed time and the illuminance value of the eye during observation of the eye, wherein t is the elapsed time, and wherein $\alpha$, $\beta$, $\gamma$, and $\tau$ are arbitrary constants obtained from experimental values; and exposure control means for determining at least one of a light intensity of the image pickup illumination light source and the amplifying ratio of the image pickup means at a time when the image pickup illumination light source emits after stopping the illumination of the eye by the observation illumination light source, on a basis of the calculated predicting formula.

2. An ophthalmologic image pickup apparatus according to claim 1, wherein the calculation means calculates the predicting formula by normalizing the detected illuminance value of the eye using an illuminance normalized curve of the eye to be examined, which is prepared in advance.

3. A method of picking up a fundus image using an ophthalmologic image pickup apparatus, comprising:

infusing a fluorescent agent into a person to be examined and starting a time C measurement using a timer of the ophthalmologic image pickup apparatus;

calculating a predicting formula:

$$\alpha \times \beta^{-\gamma(t-\tau)}$$

relating a characteristic of fluorescent illuminance to an elapsed time, of an eye to be examined from an amplifying ratio of the ophthalmologic image pickup apparatus and a measurement value of the timer, wherein t is the elapsed time, and wherein $\alpha$, $\beta$, $\gamma$, and $\tau$ are arbitrary constants obtained from experimental values; and determining at least one of the amplifying ratio and a light emission intensity of an image pickup light source at a time when starting illumination of the fundus after stopping illumination of the eye for observation based on the calculated predicting formula.

* * * * *